(12) United States Patent
Demianovich

(10) Patent No.: US 8,976,934 B2
(45) Date of Patent: Mar. 10, 2015

(54) RADIATION APERTURES FOR X-RAY COLLIMATORS

(75) Inventor: Nicholas Demianovich, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 343 days.

(21) Appl. No.: 13/527,328

(22) Filed: Jun. 19, 2012

(65) Prior Publication Data

US 2013/0336448 A1 Dec. 19, 2013

(51) Int. Cl.
*G21K 1/02* (2006.01)

(52) U.S. Cl.
USPC .......................................... 378/147

(58) Field of Classification Search
CPC ............... G21K 1/02; G21K 1/04; A61B 6/06
USPC ................................. 378/147, 150
See application file for complete search history.

(56) References Cited

U.S. PATENT DOCUMENTS

| | | |
|---|---|---|
| 4,489,426 A | 12/1984 | Grass et al. |
| 5,237,599 A * | 8/1993 | Gunji et al. .................... 378/148 |
| 5,644,614 A | 7/1997 | Toth et al. |
| 5,866,914 A | 2/1999 | Jones |
| 6,359,958 B2 * | 3/2002 | Toth ................................ 378/19 |
| 7,170,975 B2 | 1/2007 | Distler et al. |
| 7,317,786 B2 * | 1/2008 | Distler et al. .................. 378/150 |
| 8,699,659 B2 * | 4/2014 | Ikhlef ............................. 378/19 |

* cited by examiner

*Primary Examiner* — Jurie Yun
(74) *Attorney, Agent, or Firm* — The Small Patent Law Group LLC; Dean Small

(57) ABSTRACT

A collimator includes an x-ray blocking surface including one or more generally flat plates defining an aperture edge. The aperture edge includes a first end portion including a first end of the aperture edge, a second end portion including a second end of the aperture edge, and a central portion including a center of the aperture edge. The first end portion of the aperture edge corresponds to a first end portion of a detector, the second end portion of the aperture edge corresponds to a second end portion of the detector, and the central portion of the aperture edge corresponds to a central portion of the detector. A profile of the aperture edge is discontinuous at a point between the first end of the aperture edge and the center of the aperture edge.

21 Claims, 7 Drawing Sheets

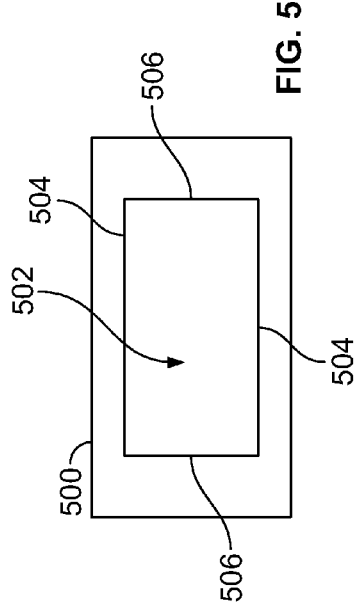
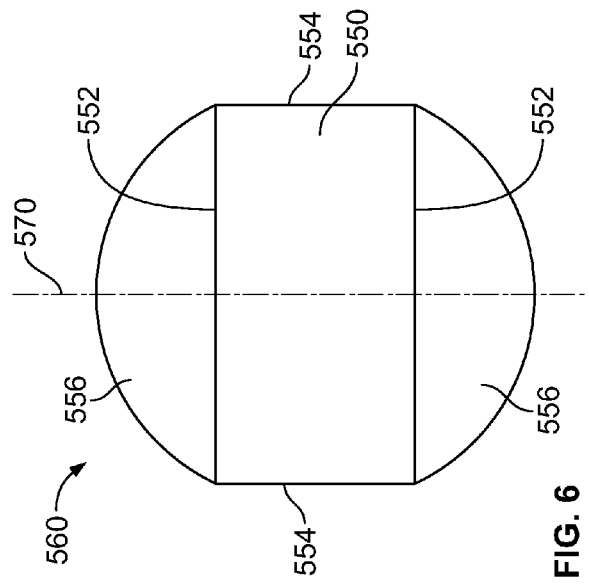
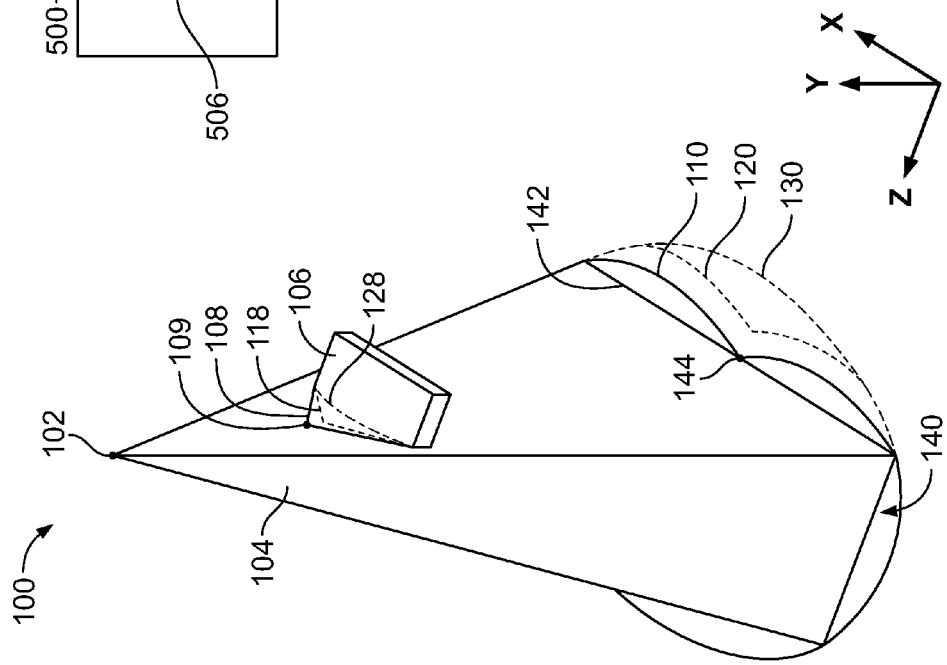

RADIATION APERTURES FOR X-RAY COLLIMATORS

BACKGROUND OF THE INVENTION

This subject matter disclosed herein relates generally to imaging systems, and more particularly, to apertures for an x-ray collimator.

Non-invasive imaging broadly encompasses techniques for generating images of the internal structures or regions of a person or object. One such imaging technique is known as x-ray computed tomography (CT). CT imaging systems measure the attenuation of x-ray beams that pass through the object from numerous angles (often referred to as projection data). Based upon these measurements, a computer is able to process and reconstruct images of the portions of the object responsible for the radiation attenuation.

Collimators are used to filter a stream of rays from a source (such as an x-ray tube) so that the rays traveling in a desired direction or directions are allowed to pass through. The collimator may be made from a material that substantially blocks x-rays, with an aperture provided to allow a portion of the x-ray beams to pass through. For example, a system may include a source and a detector. For good image reconstruction, it is desirable that all or a given portion of a detector be uniformly covered by x-rays from the source.

Certain CT systems use detectors that are generally rectangular in shape, but that curve with respect to a plane that is transverse to the x-ray beam. Use of a substantially planar collimator with a generally rectangular aperture profile to shape an x-ray beam to project on such a curved detector can result in undesirable beam projection coverage of the detector. The beam projection through the flat aperture results in a distortion (a different shape than that of the aperture) on a curved detector. This distortion reduces the dose efficiency of the system. This additional portion of the beam extending beyond the usable (or desired to be used) portion of the detector results in a patient being exposed to un-used x-rays, or an additional dose.

Certain known CT systems have attempted to address this issue in various ways. For example, collimators that are curved along a length thereof instead of being substantially planar have been employed. These designs, however take up significantly more space than a substantially planar aperture, with space often being at a premium in CT systems (for example, space occupied by a collimator can be a limiting factor on size of bore). Also, for example, apertures with linear ramps extending from edge to center have been employed. While these linearly ramped apertures reduce the overdose when compared to rectilinear aperture shapes, linearly ramped apertures still result in un-used x-ray beam portions.

Thus, presently known collimators occupy too much space, and/or result in an undesired overdose of x-ray exposure, and/or limit or inhibit functionality.

BRIEF DESCRIPTION OF THE INVENTION

In one embodiment, a collimator is provided. The collimator includes an x-ray blocking surface that comprises one or more generally flat plates defining an aperture edge of the aperture. The aperture edge includes a first end portion including a first end of the aperture edge, a second end portion including a second end of the aperture edge, and a central portion including a center of the aperture edge. The central portion is interposed between the first and second end portions. The first end portion of the aperture edge corresponds to a first end portion of a detector, the second end portion of the aperture edge corresponds to a second end portion of the detector, and the central portion of the aperture edge corresponds to a central portion of the detector. A profile of the aperture edge is discontinuous at a point between the first end of the aperture edge and the center of the aperture edge.

In another embodiment, a system is provided. The system includes an x-ray source, a detector, and a collimator. The x-ray source provides an x-ray beam, and the detector receives a portion of the x-ray beam. The collimator is interposed between the detector and the x-ray source. The collimator includes an x-ray blocking surface that comprises one or more generally flat plates defining an aperture edge of the aperture. The x-ray blocking surface is configured so that the one or more generally flat plates prevent x-ray transmission and the aperture allows x-ray transmission therethrough, wherein a projection of the beam is projected proximate to the detector. The aperture edge includes a first end portion including a first end of the aperture edge, a second end portion including a second end of the aperture edge, and a central portion including a center of the aperture edge. The central portion is interposed between the first and second end portions. The first end portion of the aperture edge corresponds to a first end portion of a detector, the second end portion of the aperture edge corresponds to a second end portion of the detector, and the central portion of the aperture edge corresponds to a central portion of the detector. A profile of the aperture edge is discontinuous at a point between the first end of the aperture edge and the center of the aperture edge.

In a further embodiment, a system is provided. The system includes an x-ray source, a detector, a collimator, and a processor. The x-ray source provides an x-ray beam, and the detector receives a portion of the x-ray beam. The collimator is interposed between the detector and the x-ray source. The collimator includes an x-ray blocking surface that comprises one or more generally flat plates defining an aperture edge of the aperture. The x-ray blocking surface is configured so that the one or more generally flat plates prevent x-ray transmission and the aperture allows x-ray transmission therethrough, wherein a projection of the beam is projected proximate to the detector. The aperture edge includes a first end portion including a first end of the aperture edge, a second end portion including a second end of the aperture edge, and a central portion including a center of the aperture edge, the central portion interposed between the first and second end portions. The first end portion of the aperture edge corresponds to a first end portion of the detector, the second end portion of the aperture edge corresponds to a second end portion of the detector, and the central portion of the aperture edge corresponds to a central portion of the detector. The central portion of the aperture edge is configured to provide a first beam projection portion substantially conforming with a profile of the central portion of the detector, and the first end portion of the aperture edge is configured to provide a second beam projection portion substantially differing with a profile of the first end portion of the detector. The processor is configured to reconstruct an image using information provided by the detector, wherein information provided by the central portion of the detector is processed in a first manner including reconstruction of an image and information provided by the first end portion of the detector is processed in a second manner including tracking processing.

BRIEF DESCRIPTION OF THE DRAWINGS

FIG. 4 illustrates a collimator system and resulting overdose of x-rays.

FIG. 5 illustrates a collimator with a generally flat, or rectilinear, aperture.

FIG. 6 illustrates the resulting projection of the aperture of FIG. 5.

DETAILED DESCRIPTION OF THE INVENTION

Figure 1:
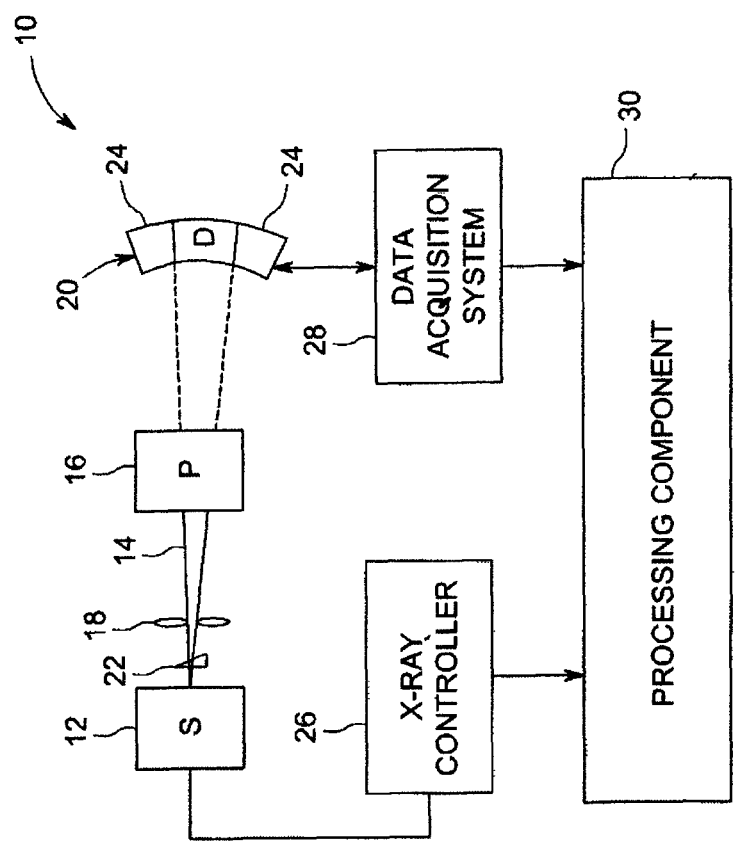
FIG. 1 is a simplified block diagram of a computed tomography (CT) imaging system that is formed in accordance with various embodiments.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

Embodiments provide a generally planar aperture having an opening curvature tuned for a given system geometry. For example, the opening curvature in some embodiments has a greater width towards the ends of the aperture which projects a substantially straight line for a curved detector. Various embodiments provide a one-piece design having improved tolerance control and compactness. Certain embodiments may be used as a primary beam limiting aperture, while certain other embodiments may be used as a secondary aperture to reduce scatter. Various embodiments provide a relatively simple aperture edge shape, such as, for example, a radius, while certain other embodiments provide more complex geometries such as, for example, a series of differing edge profiles. For example, in certain embodiments, a complex aperture edge is provided which results in a linear projection in an imaging space and a non-linear projection outside of the imaging space. The non-linear projection outside of the imaging space may be used, for example, for tracking. A technical effect of various embodiments is to provide improved shaping of x-ray beams and/or improved x-ray dosage management and/or ease of manufacturing and/or customizable shaping and/or improved form factor (e.g. requiring less space).

FIG. 1 is a simplified block diagram of a computed tomography (CT) imaging system 10 that is formed in accordance with various embodiments. The imaging system 10 may be utilized to acquire x-ray attenuation data at a variety of views around a volume undergoing imaging (e.g., a patient, package, manufactured part, and so forth). The imaging system 10 includes an x-ray source 12 that is configured to emit radiation, e.g., x-rays 14, through a volume containing a subject 16, e.g. a patient being imaged.

In the embodiment shown in FIG. 1, the imaging system 10 includes a collimator 18. In operation, the emitted x-rays 14 pass through an opening, or aperture of the collimator 18 which limits the angular range associated with the x-rays 14 passing through the volume in one or more dimensions (certain apertures formed in accordance with various embodiments are discussed in more detail below). More specifically, the collimator 18 shapes the emitted x-rays 14, such as to a generally cone or generally fan shaped beam that passes into and through the imaging volume in which the subject or object of the imaging process, e.g., the subject 16, is positioned. In embodiments, the collimator 18 may be adjusted to accommodate different scan modes, such as to provide a narrow fan-shaped x-ray beam in a helical scan mode and a wider cone-shaped x-ray beam in an axial scan mode. The collimator 18 may be formed, for example, from a plate with an aperture formed therethrough. Optionally, the collimator 18 may be formed using two or more translating plates or shutters.

The imaging system 10 also includes a filter 22 that is disposed between the x-ray source 12 and the collimator 18. In various embodiments, the filter 22 is a bowtie filter having a predetermined thickness and fabricated from a predetermined material. In operation, the x-rays 14 pass through the filter 22 which adjusts a frequency and/or an intensity characteristic of the emitted x-rays 14. The filter 22 may be a conventional bowtie filter or other X-ray beam shaping filter suitable for varying the intensity of the beam of x-rays 14 to compensate for different thicknesses of the subject 16 as seen from different angular positions of the x-ray source 12. In one embodiment, the thickness of the bowtie filter 22 may vary in the axial direction to compensate for the Heel effect. Optionally, a separate or additional filter having a thickness that varies in the axial direction may be provided in conjunction with the bowtie filter 22 to compensate for the Heel effect.

In operation, the x-rays 14 pass through or around the subject 16 and impinge the detector 20. In the illustrated embodiment, the detector is shown curved along a direction generally transverse to the x-rays 14. The detector 20 includes a plurality of detector elements 24 that may be arranged in a single row or a plurality of rows to form an array of detector elements 24. The detector elements 24 generate electrical signals that represent the intensity of the incident x-rays 14. The electrical signals are acquired and processed to reconstruct images of one or more features or structures within the subject 16. In various embodiments, the imaging system 10 may also include an anti-scatter grid (not shown) to absorb or otherwise prevent x-ray photons that have been deflected or scattered in the imaging volume from impinging the detector 20. The anti-scatter grid may be a one-dimensional or two-dimensional grid and/or may include multiple sections, some of which are one-dimensional and some of which are two-dimensional.

The imaging system 10 also includes an x-ray controller 26 that is configured to provide power and timing signals to the x-ray source 12. The imaging system 10 further includes a data acquisition system 28. In operation, the data acquisition system 28 receives data collected by readout electronics of the detector 20. The data acquisition system 28 may receive sampled analog signals from the detector 20 and convert the data to digital signals for subsequent processing by a processor 30. Optionally, the digital-to-analog conversion may be performed by circuitry provided on the detector 20.

The processor 30 is programmed to perform functions described herein, and as used herein, the term processor is not limited to just integrated circuits referred to in the art as computers, but broadly refers to computers, microcontrollers, microcomputers, programmable logic controllers, application specific integrated circuits, and other programmable circuits, and these terms are used interchangeably herein.

Figure 2:
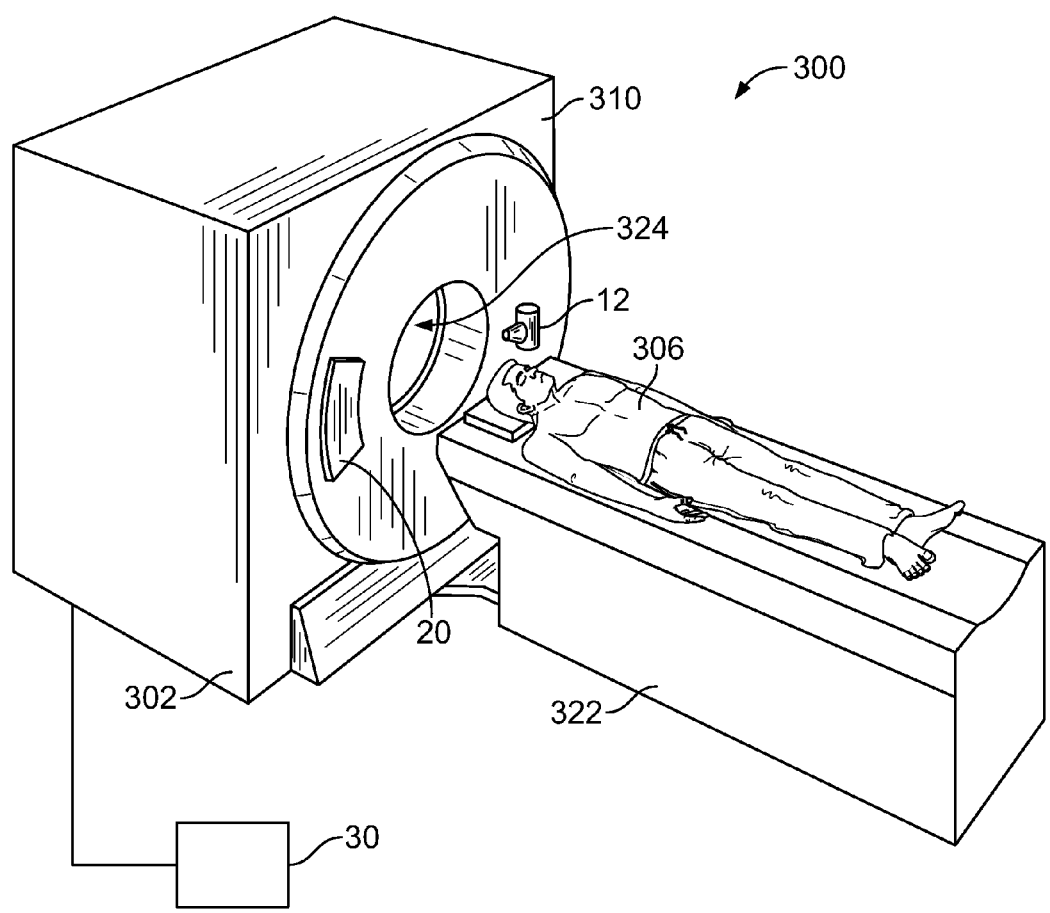
FIG. 2 is a pictorial view of an imaging system that is formed in accordance with various embodiments.
Figure 3:
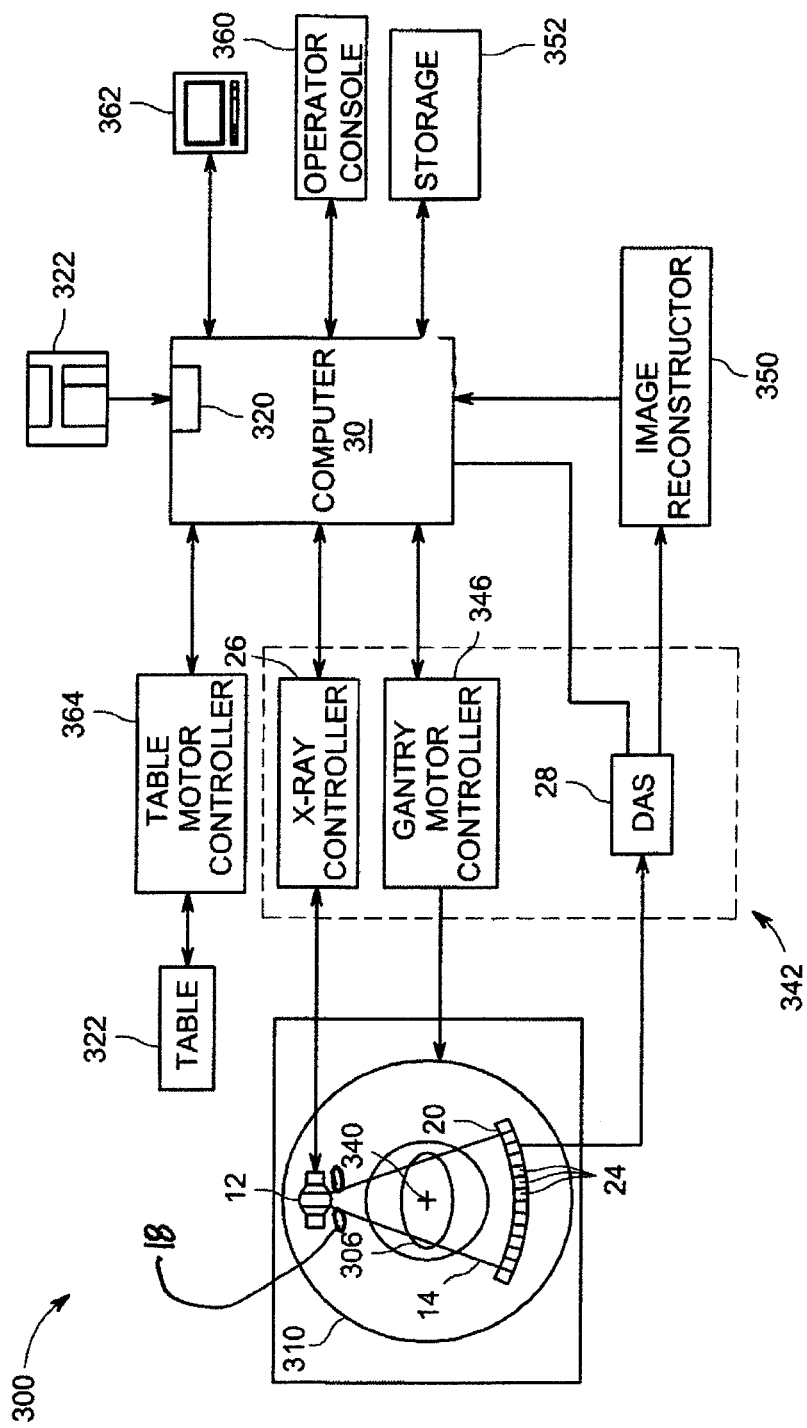
FIG. 3 is a block schematic diagram of a portion of the imaging system shown in FIG. 2.

FIG. 2 is a pictorial view of an imaging system 400 that is formed in accordance with various embodiments. FIG. 3 is a block schematic diagram of a portion of the imaging system 400 shown in FIG. 2. Although various embodiments are described in the context of an imaging system that includes a CT imaging system, it should be understood that other imaging systems capable of performing the functions described herein are contemplated as being used.

The imaging system 300 is illustrated, and includes a CT imaging system 302. Optionally, modalities other than CT may be employed with the imaging system 300. For example, the imaging system 300 may be a standalone CT imaging system, an x-ray imaging system, and/or a CT system for a dedicated purpose such as extremity or breast scanning, and combinations thereof, among others. The imaging system 300 also may be a multi-modality imaging system.

The CT imaging system 302 includes a gantry 310 that has the x-ray source 12 that projects a beam of x-rays 14 toward the detector array 20 on the opposite side of the gantry 310. The detector array 20 includes the plurality of detector elements 24 that are arranged in rows and channels that together sense the projected x-rays that pass through an object, such as the subject 306. The imaging system 300 also includes the computer 30 that receives the projection data from the detector array 20 and processes the projection data to reconstruct an image of the subject 306. In operation, operator supplied commands and parameters are used by the computer 30 to provide control signals and information to reposition a motorized table 322. More specifically, the motorized table 322 is utilized to move the subject 306 into and out of the gantry 310. Particularly, the table 322 moves at least a portion of the subject 306 through a gantry opening 324 that extends through the gantry 310.

As discussed above, the detector 20 includes a plurality of detector elements 24. Each detector element 24 produces an electrical signal, or output, that represents the intensity of an impinging x-ray beam and hence allows estimation of the attenuation of the beam as it passes through the subject 306. During a scan to acquire the x-ray projection data, the gantry 310 and the components mounted thereon rotate about a center of rotation 340. FIG. 3 shows only a single row of detector elements 24 (i.e., a detector row). However, the multislice detector array 20 includes a plurality of parallel detector rows of detector elements 24 such that projection data corresponding to a plurality of slices can be acquired simultaneously during a scan.

Rotation of the gantry 310 and the operation of the x-ray source 12 are governed by a control mechanism 342. The control mechanism 342 includes the x-ray controller 26 that provides power and timing signals to the x-ray source 12 and a gantry motor controller 346 that controls the rotational speed and position of the gantry 310. The data acquisition system (DAS) 28 in the control mechanism 342 samples analog data from detector elements 24 and converts the data to digital signals for subsequent processing. An image reconstructor 350 receives the sampled and digitized x-ray data from the DAS 28 and performs high-speed image reconstruction. The reconstructed images are input to the computer 30 that stores the image in a storage device 352. Optionally, the computer 30 may receive the sampled and digitized x-ray data from the DAS 28 and perform various methods described herein. The computer 30 also receives commands and scanning parameters from an operator via a console 360 that has a keyboard. An associated visual display unit 362 allows the operator to observe the reconstructed image and other data from computer.

The operator supplied commands and parameters are used by the computer 30 to provide control signals and information to the DAS 28, the x-ray controller 26 and the gantry motor controller 346. In addition, the computer 30 operates a table motor controller 364 that controls the motorized table 322 to position the subject 306 in the gantry 310. Particularly, the table 322 moves at least a portion of the subject 306 through the gantry opening 324 as shown in FIG. 2.

Referring again to FIG. 3, in one embodiment, the computer 30 includes a device 370, for example, a floppy disk drive, CD-ROM drive, DVD drive, magnetic optical disk (MOD) device, or any other digital device including a network connecting device such as an Ethernet device for reading instructions and/or data from a non-transitory computer-readable medium 372, such as a floppy disk, a CD-ROM, a DVD or an other digital source such as a network or the Internet, as well as yet to be developed digital means. In another embodiment, the computer 30 executes instructions stored in firmware (not shown). The computer 30 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the x-ray source 12 and the detector array 20 are rotated with the gantry 310 within the imaging plane and around the subject 306 to be imaged such that the angle at which an x-ray beam 374 intersects the subject 306 constantly changes. A group of x-ray attenuation measurements, i.e., projection data, from the detector array 20 at one gantry angle is referred to as a "view". A "scan" of the subject 306 comprises a set of views made at different gantry angles, or view angles, during one revolution of the x-ray source 12 and the detector 20. In a CT scan, the projection data is processed to reconstruct an image that corresponds to a two dimensional slice taken through the subject 306.

Exemplary embodiments of an imaging system are described above in detail. The imaging system components illustrated are not limited to the specific embodiments described herein, but rather, components of each imaging system may be utilized independently and separately from other components described herein. For example, the imaging system components described above may also be used in combination with other imaging systems.

The collimator in such a system is used, for example, to help manage the dosage of x-rays received by a patient. For example, x-rays that pass through a patient, but are not projected onto a detector, or a portion of the detector used for imaging, may be considered an overdose. In systems utilizing a flat collimator with a rectilinear or linearly sloped aperture shape along with a detector that is curved with respect to a plane defined by the flat collimator, an overdose, or poor dose management, may result due to the geometry of the system. FIG. 4 illustrates a collimator system 100 and resulting overdose of x-rays.

The collimator system 100 includes an x-ray source 102, a collimator 106 and a detector 140. A beam 104 emanating from the source 102 passes by the collimator 106 and projects generally toward the detector 140. In FIG. 4, the source 102 is modeled as a point source, however tube sources may be used. Further, a single collimator is shown. In embodiments, additional filters and/or collimators may be used. In FIG. 4, the collimator 106 is depicted as a single plate disposed on one side of the beam 104. A generally symmetric collimator plate may also be employed on an opposing side of the beam 104. While the detector 140 is curved along the x-direction of FIG. 4, the detector and projection of x-ray beam proximate to the detector 140 are illustrated as a horizontal projection. The detector 140 is generally rectangular in shape and includes a lateral side 142.

The shape of the aperture defined by the collimator limits or defines the shape of the projection of the fan beam 104 onto and near the detector 140. For example, for a collimator 106 having a generally flat edge 128 (shown in phantom line in FIG. 4), the resulting beam projection, 130 (also shown in phantom line in FIG. 4) extends laterally past the lateral side 142 of the detector 140 as shown. The portion of the projection 130 extending past the lateral side 142 is generally considered an overdose of x-ray, as the patient is exposed to that portion, but the portion is not used by the system, for example, in reconstructing an image.

Certain previously known systems have attempted to provide beam projections that reduce the overdose, and improve dose management. By reducing a width of the aperture at a center line of the aperture (and corresponding center line of the detector), the area of the portion or portions of the projection projecting beyond the detector may be reduced. For example, in FIG. 4, a sloped profile 118 (shown in dashed line) for the collimator is also shown. The resulting projection 120 (shown in dashed line) corresponding to profile 118 is closer to the lateral side 142 along the center line of the detector than the projection 130 resulting from a flat edge 128. The portions of the projection 120 extending beyond the detector also take up less area than those for the projection 130, resulting in better dose management.

By bringing the peak of the sloped profile 118 laterally inward, the peak of the sloped profile may be located tangent to the detector projection line (a line extending from the source to the lateral edge of the detector at the detector center line). This is shown in FIG. 4 as a sloped profile 108 having a peak 109 located along the center line of the collimator 106 and projector 140. Projection 110 results from use of the sloped profile 108. The sloped profile 108 and the peak 109 are sized and configured so that the projection 110 does not extend substantially past the detector 140 at the center 144 of the lateral side 142 of the detector 140. If a similar sloped profile 108 were used on the opposing side of the beam 104, the resulting width of the projection 110 across the center line of the detector 140 (through the center 144 of the lateral side 142) would match the width of the detector in the z-direction. Thus, the beam width may be defined by the center of the aperture for a sloped profile such as sloped profile 108, or may be defined by the end points of the aperture for a flat aperture such as one having a generally flat edge 128.

The above described aperture shapes are also discussed in connection with FIGS. 5a and 5b as well as FIGS. 6a and 6b. FIG. 5 depicts a collimator 500 with a generally flat, or rectilinear, aperture 502, and FIG. 6 depicts the resulting projection 560 of the aperture 502 on a detector that is curved along a direction substantially parallel to the collimator 500 (or transverse to a beam passing through the collimator 500). The collimator 500 is made of an appropriate material of sufficient width to allow for substantial prevention of the passage of x-rays through the solid portions of the collimator 500, and the aperture 502 is an opening extending through the thickness of the collimator 500 (into the page, in FIG. 5) configured to allow passage of x-rays.

The aperture 502 is substantially rectilinear. The aperture has sides 504 that extend along the length of the aperture 502 and ends 506 that extend along width of the aperture 502. In FIG. 5, the sides 504 are flat, and are not sloped or angled with respect to corresponding sides of a rectilinear detector.

FIG. 6 depicts the projection 560 resulting from passage of an x-ray beam through the aperture 502. The projection 560 is shown with respect to a detector 550. The detector 550 is rectilinear in shape, having sides 552 that extend along the length of the detector 550 and ends 554 that extend across the width of the detector 550. The width of the aperture 502 is configured so that the width of the projection 560 substantially matches the width of the detector 550 at the ends 554 of the detector. Thus, as discussed above, the projection 560 extends laterally beyond the detector 550, with a maximum distance of extension along the center line 570 of the detector 550. The projection 560 includes portions 556 that extend beyond the detector 550, representing excessive dosage of an x-ray.

Figure 8:
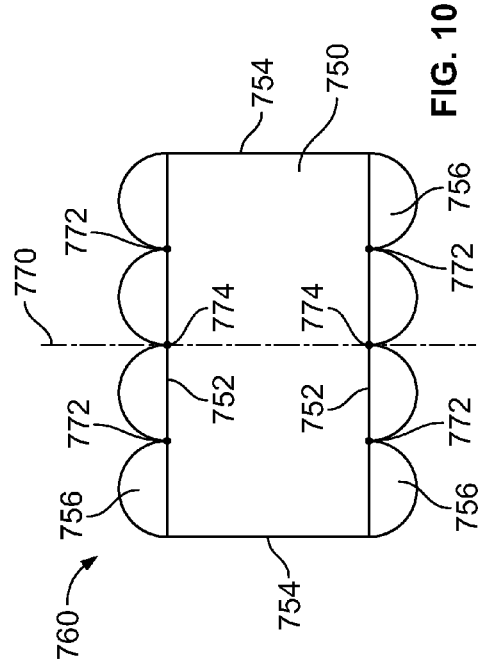
FIG. 8 illustrates the resulting projection of the aperture of FIG. 7.
Figure 7:
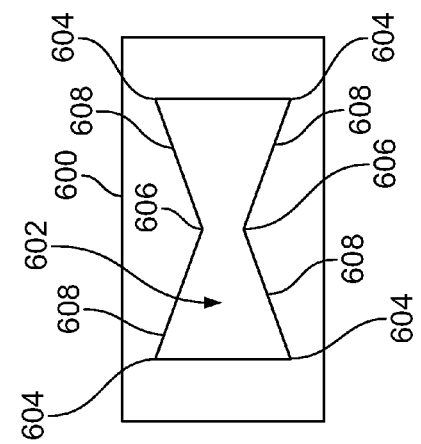
FIG. 7 illustrates a collimator with an aperture having a linear taper.

FIG. 7 depicts a collimator 600 with a tapered, aperture 602, and FIG. 8 depicts the resulting projection 660 of the aperture 602 on a detector that is curved along a direction substantially parallel to the collimator 600 (or transverse to a beam passing through the collimator 600). The collimator 600 is made of an appropriate material of sufficient width to allow for substantial prevention of the passage of x-rays through the solid portions of the collimator 600, and the aperture 602 is an opening extending through the thickness of the collimator 600 (into the page, in the sense of FIG. 6) configured to allow passage of x-rays.

The aperture 602 includes an edge having a linear taper. The aperture 602 has lateral edges defined by end points 604 and center points 606. The edge tapers inward laterally and inward along the length of the aperture 602 from the end points 604 to the center points 606 along continuous sloped lines 608. Thus, the sides of the aperture 602 are not flat, and instead are sloped or angled with respect to corresponding sides of a rectilinear detector.

FIG. 8 depicts the projection 660 resulting from passage of an x-ray beam through the aperture 602. The projection 660 is shown with respect to a detector 650. The detector 650 is rectilinear in shape, having sides 652 that extend along the length of the detector 650 and ends 654 that extend across the width of the detector 650. The width of the ends of the aperture 602 is configured so that the width of the projection 660 substantially matches the width of the detector 650 at the ends 654 of the detector at a given distance from the source, and the width between the center points 606 is configured so that the width of the projection 660 at the center line 670 substantially matches the width of the detector 650 at the given distance. Thus, as discussed above, the projection 660 extends laterally beyond the detector 650, and includes portions 656 that extend beyond the detector 650, representing excessive dosage of an x-ray.

Various embodiments provide for improved dosage management by more closely correlating the shape of the projection, or beam projection, to a detector shape than is provided by, for example, the above described flat and/or linear taper profiles. For example, FIG. 9 depicts a collimator 700 with an aperture 702 including a plurality of points along a lateral edge that are tangent to a projection line of a detector, and FIG. 10 depicts the resulting projection 760 of the aperture 702 on a detector curved along a direction substantially parallel to the collimator 700 (or transverse to a beam passing through the collimator 700).

Figure 10:
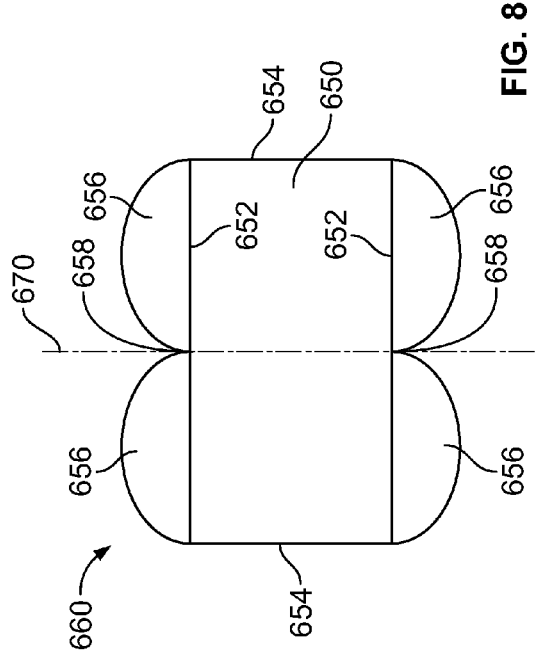
FIG. 10 illustrates the resulting projection of the aperture of FIG. 9.
Figure 9:
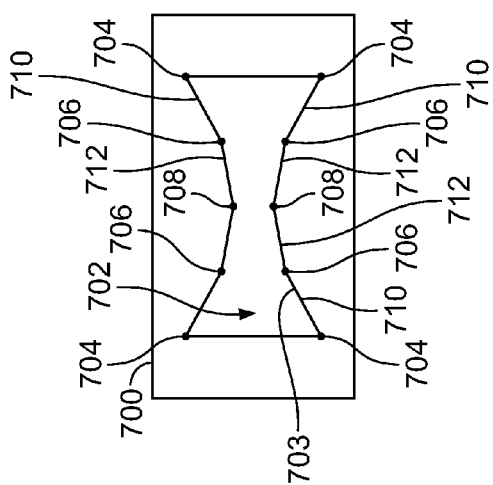
FIG. 9 illustrates a collimator formed in accordance with various embodiments.

FIG. 9 depicts a collimator 700 with an aperture 702 having an aperture edge 703, and FIG. 10 depicts the resulting projection 760 of the aperture 702 on a detector curved along a direction substantially parallel to the collimator 700 (or transverse to a beam passing through the collimator 700). The collimator 700 is made of an appropriate material of sufficient width to allow for substantial prevention of the passage of x-rays through the solid portions of the collimator 700, thereby providing an x-ray blocking surface, and the aperture 702 is an opening extending through the thickness of the collimator 700 (into the page, in the sense of FIG. 9) configured to allow passage of x-rays.

The collimator 700 depicted in FIG. 9 is a substantially flat, or planar collimator. The collimator 700 may be made of a single plate with an aperture formed therethrough, or, as another example, the collimator 700 may include a plurality of blades, plates, or other portions that are positioned to provide a desired aperture. In some embodiments, the blades, plates or other portions may be articulable to provide for adjustability of, for example, aperture width. Further, in some embodiments, the collimator 700 may be one of a series of collimators that a beam passes through. For example, one collimator may be used to shape or direct a beam while other collimators are used to reduce scatter. The aperture shapes discussed herein may be used with one or more of such collimators used together in a system.

The aperture edge 703 of the aperture 702 includes lateral edges that include end points 704, center points 708, and intermediate points 706. The end points 704 are located at the ends of the collimator 700, and the center points 708 are located along a center line of the collimator 700. The intermediate points 706 are located along the length of the lateral edges interposed between the end points 704 and the center points 708. Each of the end points 704, intermediate points 706, and center points 708 are configured, based on system geometry and configuration, so that, for a given distance of the beam source to the detector 750, each end point 704, intermediate point 706, and center point 708 will be tangent to the detector projection line (an individual ray passing by the point will land on the lateral edge of the detector at a corresponding length along a lateral edge of the detector). Thus, each of the end points 704, intermediate points 706, and center points 708 are configured so that the width of the projection 760 at a corresponding location along the length of the detector 750 substantially matches the width of the detector 750 at the corresponding location along the length of the detector 750.

Each end point 704 is joined to an intermediate point 706 by a first line segment 710 that extends inwardly laterally along the length of the edge of the aperture 702. Also, each intermediate point 706 is joined to a center point 708 by a second line segment 712 that extends inwardly laterally along the length of the edge of the aperture 702. The slopes of the first line segment 710 and the second line segment 712 (or the angle between the first line segment 710 and the second line segment 712 and a lateral edge of the detector) are different. In FIG. 9, the aperture 702 includes two differently sloped, or discontinuous, line segments along the edge 703 between an end and the center of the collimator, and one intermediate peak point (a point at which the projection lies substantially at the edge of the detector) interposed between the center and the end of the aperture. In other embodiments, more line segments and peak points may be used.

FIG. 10 depicts the projection 760 resulting from passage of an x-ray beam through the aperture 702. The projection 760 is shown with respect to a detector 750. The detector 750 is rectilinear in shape, having sides 752 that extend along the length of the detector 750 and ends 754 that extend across the width of the detector 750. As discussed above, the width of the aperture 702 is configured so that the width of the projection 760 substantially matches the width of the detector 650 at locations along the sides 752 of the detector 750 corresponding to the end points 704, intermediate points 706, and center points 708 of the aperture 702. For example, intermediate points 772, which correspond to intermediate points 706 of the aperture 702, are points at which the projection 760 is located substantially along a lateral edge of the detector 750. Similarly, center points 774, which correspond to center points 708 of the aperture 702, are points at which the projection 760 is located substantially along a lateral edge of the detector 750. The aperture 702 thus provides a plurality of points along a length of a detector where the projection does not extend substantially past an edge of a detector. The projection 760 extends laterally beyond the detector 750 at locations between the plurality of peak points, and includes portions 756 that extend beyond the detector 750. These portions are relatively smaller than the portions of the flat or linearly tapered apertures discussed above, thus reducing excessive dosage of an x-ray.

Thus, some embodiments provide a substantially flat or planar collimator that provide a corresponding projection more closely approximating the surface of a curved rectilinear detector. Thus, various embodiments also provide reduced x-ray dosage when used with a curved detector.

Figure 12:
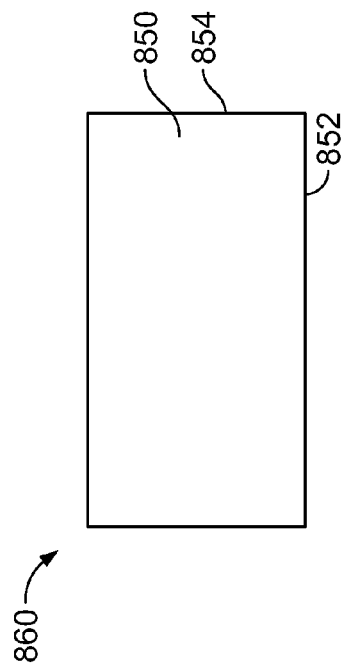
FIG. 12 illustrates the resulting projection of the aperture of FIG. 11.
Figure 11:
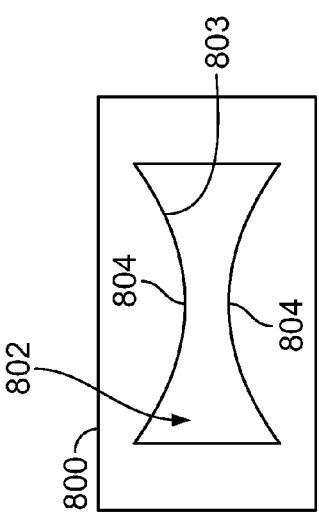
FIG. 11 illustrates a collimator formed in accordance with various embodiments.

By breaking the edge of the aperture into increasingly shorter line segments interposed between points located along tangents to the projection of a detector edge, the portions of a resulting projection extending laterally beyond a detector may be even further reduced. As the line segments become infinitesimally small, the edge profile of the aperture becomes a curve. Thus, a curve of a given profile may be considered an ideal shape to produce a projection that substantially matches a rectilinear detector. FIG. 11 depicts a collimator 800 with a radiused aperture 802 having an aperture edge 803, and FIG. 12 depicts the resulting projection 860 of the aperture 802 on a detector that is curved along a direction substantially parallel to the collimator 800 (or transverse to a beam passing through the collimator 800). The collimator 800 is made of an appropriate material of sufficient width to allow for substantial prevention of the passage of x-rays through the solid portions of the collimator 800, and the aperture 802 is an opening extending through the thickness of the collimator 800 (into the page, in the sense of FIG. 11) configured to allow passage of x-rays.

The aperture edge 803 of the aperture 802 includes opposed curved portions 804 that extend along the aperture edge 803 between the ends of the aperture 802. In the embodiment of FIGS. 8a and 8b, the aperture 802 is tuned or configured to provide a projection substantially conforming to a curved rectilinear detector for a given system geometry and configuration. Thus, for the given geometry and configuration, each point along the curved edge of the aperture 802 is substantially at a tangent to a ray from the source to an edge of the detector. As shown in FIG. 12, the detector 850 is rectilinear in shape, having sides 852 that extend along the length of the detector 850 and ends 854 that extend across the width of the detector 850. The projection 860 substantially matches the profile of the detector, reducing, minimizing, and/or eliminating excess x-ray dosage.

In alternate embodiments, the aperture 802 may be tuned to cover only a given proportion of a detector. For example, in embodiments, only a portion of the detector surface area may be used for imaging. Thus, in embodiments, the aperture 802 may be tuned so that the resulting projection covers a desired portion, for example one-half, of a detector width. In other embodiments, the same collimator and aperture may be used for different applications requiring different imaging widths used by the detector. In such embodiments, the aperture may be tuned or configured for a given imaging width (for example, a more frequently used imaging width), and then adjusted as discussed above via, for example, movable plates, to provide alternate imaging widths. Or, as another example, the aperture may be tuned or configured for a width intermediate between two widths to provide more closely matched dosage management for both widths than if the aperture were tuned specifically for one of the widths.

Thus, various embodiments provide for ideal or near ideal coverage of a given detector shape. In alternate embodiments, however, the aperture of a collimator may be configured to deviate from such ideal or near ideal coverage.

Figure 14:
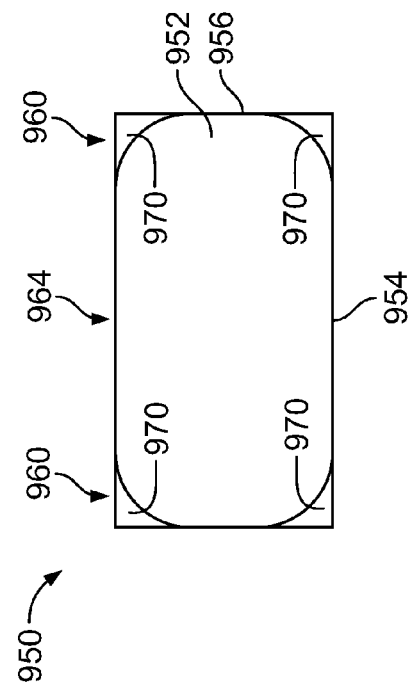
FIG. 14 illustrates the resulting projection of the aperture of FIG. 13.
Figure 13:
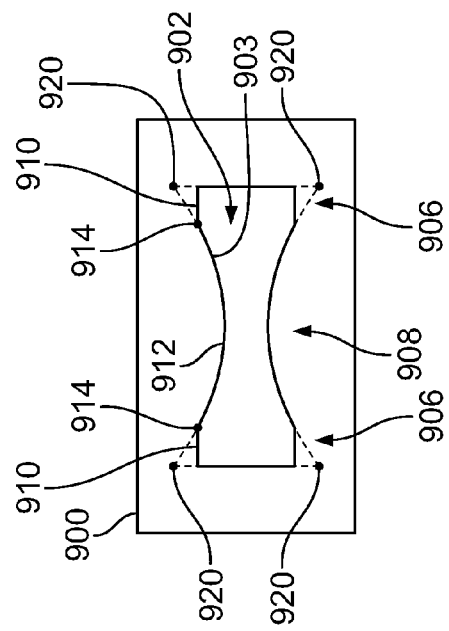
FIG. 13 illustrates a collimator formed in accordance with various embodiments.

For example, FIG. 13 illustrates a collimator 900 formed in accordance with an embodiment. The collimator 900 includes an aperture 902 having an aperture edge 903. In the embodiment of FIG. 9, the aperture 902 is tuned or configured so that a first portion of the resulting projection substantially matches the profile of a detector, and so that a second portion of the resulting projection substantially differs from the profile of the detector. FIG. 14 depicts the resulting projection 950 of the aperture 902 on a detector 952 that is curved along a direction substantially parallel to the collimator 900 (or transverse to a beam passing through the collimator 900). The collimator 900 is made of an appropriate material of sufficient width to allow for substantial prevention of the passage of x-rays through the solid portions of the collimator 900, and the aperture 902 is an opening extending through the thickness of the collimator 900 (into the page, in the sense of FIG. 13) configured to allow passage of x-rays.

As shown in FIG. 13, the aperture edge 903 of the aperture 902 includes a central portion 908 interposed between end portions 906. The central portion 908 corresponds to a central portion of a detector, while the end portions 906 correspond to the end portions of a detector. The aperture 902 is configured to provide a beam projection substantially matching the profile of the detector over the central portion, but deviating from the profile over the end portions. In the illustrated embodiments, with the detector being substantially rectilinear and curved with respect to a plane generally parallel to a plane defined by the collimator 900, the central portion 908 of the aperture 912 comprises a curved portion 912. The curved portion 912 is tuned or configured to provide an ideal or near ideal projection for covering a detector having a given width (or for covering a given portion of a detector width). The curved portion 912 provides a substantially linear beam projection corresponding to the central portion of a corresponding rectilinear detector.

The end portions 906 of the aperture 902 include a flat portion 910. As used herein in connection with aperture profiles, the term flat means generally parallel to a side or edge of a substantially rectilinear detector. The flat portion 910 joins the curved portion 912 at point 914, representing a discontinuity between the flat portion 910 and the curved portion 912 along the edge 903 of the aperture 902. The flat portion 910 is located laterally inwardly from the intersection of extensions of the curved portion 912 and an edge of the aperture 902 indicated at point 920. Thus, the aperture 902 is smaller in area than an aperture tuned to substantially match the profile of the detector over the length of the detector. The projection resulting from aperture 902 therefore covers less area than the detector profile. The flat portion 910 thus is configured to provide a beam projection that extends laterally inwardly from the substantially linear beam projection provided by the curved portion 912.

FIG. 14 depicts the projection 950 resulting from the aperture 902 with respect to a substantially rectilinear detector 952. The detector 952 is rectilinear in shape, having sides 954 that extend along the length of the detector 952 and ends 956 that extend across the width of the detector 952. The projection 950 substantially matches the profile of the detector along a central portion 964 of the detector 952 corresponding to the central portion 908 of the aperture 902, thereby reducing, minimizing, and/or eliminating excess x-ray dosage while providing coverage of the available imaging space for the central portion 964.

However, because of the configuration of the end portions 906 discussed above, the projection 950 does not extend across the full width of the detector 952 proximate to the end portions 960 of the detector 952. Instead, the detector 952 includes portions 970 that are not covered by the projection 950. For example, in embodiments, not all of the detector area may be utilized or required for imaging, and thus the entire detector area may not need to receive a portion of a beam. In certain embodiments, portions of the detector may be used for tracking purposes, for example, as discussed below, and the aperture may be tuned to provide improved tracking along one or more edges of a detector.

Further, in alternate embodiments, different shapes, other than the flat portion, may be employed on one or more end portions of an aperture. For example, linear slopes, steps, or curves differing from a curved central portion may be included in alternate embodiments. In the embodiment of FIG. 13, the end portions are symmetric about the center of the aperture. In alternate embodiments, the end portions may be asymmetric.

Figure 15:
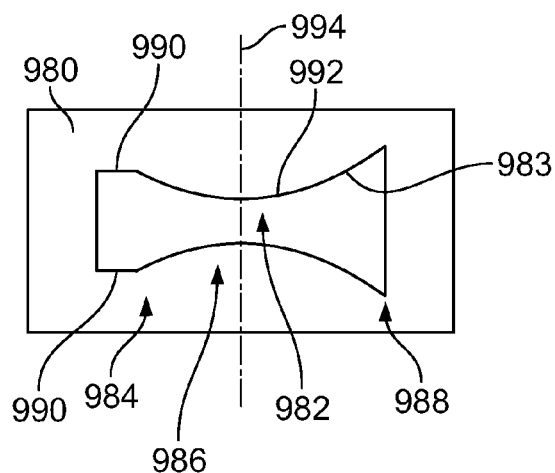
FIG. 15 illustrates a collimator having an asymmetric aperture formed in accordance with various embodiments.

FIG. 15 illustrates a collimator 980 having an asymmetric aperture 982 having an aperture edge 983 formed in accordance with an embodiment. The illustrated embodiment is asymmetric about a center line 994 bisecting the length of the collimator 980. Additionally or alternatively, the aperture may be asymmetric about other axes as well, such as an axis bisecting the width of the collimator. The aperture edge 983 of the aperture 982 includes a first end 984 and a second end 988. A center portion 986 is interposed between the first end 984 and the second end 988. The center portion 986 includes a curved portion 992 that is tuned or configured to provide a projection substantially coinciding with a curved rectilinear detector profile. The curved portion 992 of the edge of the aperture 982 extends continuously through the center portion 986 as well as to the second end 988.

However, the first end 984 includes a flat portion 990 of the edge 983 of the aperture 982, and the edge 983 of the aperture 982 is discontinuous where the flat portion 990 joins the curved portion 992 (see, e.g., discussion above regarding flat portion 910). For a detector having a curved rectilinear profile for which the aperture 982 was tuned or configured, the resulting projection of the aperture 982 would substantially coincide with the detector profile for the portion of the detector corresponding to the center portion 986 and the second end 988. However, for the portion of the detector corresponding to the first end 984 of the aperture 982, the resulting projection would not substantially coincide with the profile of the detector, instead resulting in portions of the detector not being covered by the projection (see, e.g., discussion above regarding portions 970).

Figure 16:
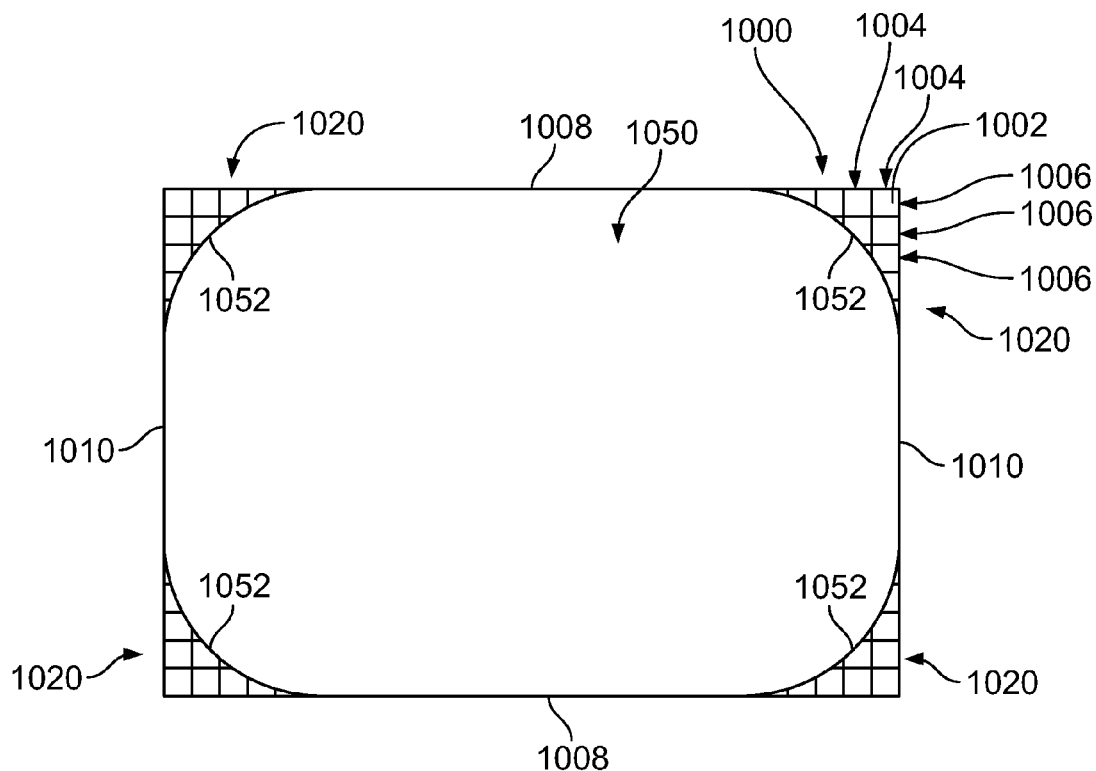
FIG. 16 illustrates an projection projected on a detector resulting from an aperture formed in accordance with an embodiment.

FIG. 16 illustrates a projection 1050 projected on a detector 1000 resulting from an aperture formed in accordance with an embodiment. For example, the detector 1000 is a curved rectilinear detector, and an aperture generally similar to the aperture 902 may be employed, with the aperture including a curved center portion configured to provide a projection substantially matching the profile of the detector 1000, and flat portions positioned at the ends of the aperture to provide a projection that does not substantially match the profile of the detector 1000 toward the ends of the detector 1000.

The detector 1000 includes sides 1008 extending along the length of the detector 1000 and ends 1010 extending along the width of the detector 1000. The detector 1000 is generally rectilinear in shape, and is curved with respect to a plane transverse to the beam being projected on to the detector 1000. The detector includes a plurality of detector elements 1002 arranged in rows 1004 and channels 1006. As shown in FIG. 16, the detector 1000 includes portions defined by boundaries 1052 that are not covered by the projection. The boundaries 1052 are located proximate to the edges of the detector 1000. Thus, a subgroup of elements 1020 are defined that either are not exposed to the beam, or are only partially exposed to the beam, with only a portion of the element exposed to the beam.

In embodiments, all or some of the subgroup of elements 1020 are used for tracking purposes. For example, during a scanning process, the focal point of the beam may move relative to the collimator and/or detector. By knowing the position of the detector as well as the position of the collimator, the focal point may be determined by the location of the beam projection on the detector. Also, by providing a projection that covers less than the entirety of the detector elements, the edge or boundary of the projection may be detected and tracked by the detector. For example, the movement of one or more of the boundaries 1052 may be tracked by one or more elements of the subgroup of elements 1020, with the information regarding the movement of the boundary used to determine the location and movement of the focal point. Thus, a flux of a beam on the detector may be detected and used to determine the position and movement of a focal point of the beam. By providing an aperture that provides a boundary 1052 with a higher order contour (such as a slope or a curve), increasingly precise information regarding movement of the focal point may be provided. Thus, the movement and/or the location of the focal point may be determined from information from the subgroup of elements 1020. In some embodiments, information from one group of detectors is processed by a processor to reconstruct an image, and information from the subgroup of elements 1020 is processed by the processor for tracking and to determine any necessary adjustments to system configuration or geometry. Thus, in embodiments, differently located detector elements are processed differently.

In various embodiments, the imaging area may only require a portion of the available detector elements. In such embodiments, an aperture may be provided that provides a projection that substantially matches the desired imaging area for a portion of the detector, but that also expands beyond the desired imaging area and covers additional elements of the detector not used for imaging, with the additional elements used, for example, for tracking. In certain embodiments, the desired image area may be irregular in shape (e.g. not rectilinear), and an aperture formed in accordance with embodiments described herein may be utilized to provide an irregularly shaped projection.

Further still, for example, in some embodiments the detector may be substantially flat instead of curved, and an aperture may be provided having a first, substantially flat edge over a first portion of the aperture to provide a beam that substantially matches the profile of the detector at a first corresponding detector portion, with the aperture having a second, differently shaped (for example curved) edge that shapes a beam portion that does not match the profile of the detector at a second corresponding detector portion. In other embodiments, the desired imaging area may be only a portion of detector, and the aperture may be tuned, configured, and/or adjusted to provide a beam covering the desired imaging area.

Additionally or alternatively, some embodiments provide a system with interchangeable apertures that may be selected, or toggled between, for different applications. For example, collimators with differently sized apertures may be provided for differently sized imaging areas. As another example, one or more collimators may be provided that shape beams that substantially match a detector profile, along with one or more additional collimators that shape beams that do not substantially match a detector profile for at least a portion of the detector profile.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. In embodiments, the readable storage medium excludes signals. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A collimator comprising:
    an x-ray blocking surface comprising a one-piece plate defining an aperture formed therethrough, the aperture defining an aperture edge,
    wherein the aperture edge includes a first end portion including a first end of the aperture edge, a second end portion including a second end of the aperture edge, and a central portion including a center of the aperture edge, the central portion interposed between the first and second end portions, wherein the first end portion of the aperture edge corresponds to a first end portion of a detector, the second end portion of the aperture edge corresponds to a second end portion of the detector, and the central portion of the aperture edge corresponds to a central portion of the detector; and
    wherein a profile of the aperture edge is discontinuous at a point between the first end of the aperture edge and the center of the aperture edge.

2. The collimator of claim 1, wherein the profile of the aperture edge is discontinuous at a plurality of points between the first end of the aperture edge and the center of the aperture edge.

3. The collimator of claim 1, wherein the aperture edge comprises a linear portion and a curved portion joining the linear portion, wherein a joining point defining the location where the linear portion joins the curved portion defines a discontinuity of the aperture edge.

4. The collimator of claim 1, wherein the first end portion of the aperture edge includes a flat segment extending along a length of the aperture edge, and the central portion of the aperture edge includes a non-linear portion extending along the length of the aperture edge.

5. The collimator of claim 4, wherein the non-linear portion is configured to provide a first, substantially linear beam projection edge corresponding to the central portion of the detector, and wherein the flat segment is configured to provide a second beam projection edge that extends inwardly from the first, substantially linear beam projection in a lateral direction when the collimator is used to shape a beam for projection onto a curved detector.

6. The collimator of claim 1, wherein the aperture edge includes a plurality of differently sloped linear segments interposed between the first end of the aperture edge and the center of the aperture edge.

7. The collimator of claim 1, wherein the central portion of the aperture edge is configured to provide a first beam projection substantially conforming with a profile of the central portion of the detector, and the first end portion of the aperture edge is configured to provide a second beam projection substantially differing with a profile of the first end portion of the detector.

8. The collimator of claim 1, wherein the aperture edge is asymmetric about a center line bisecting a length of the collimator.

9. A system comprising:
    an x-ray source, the x-ray source providing an x-ray beam;
    a detector, the detector receiving a portion of the x-ray beam; and
    a collimator interposed between the detector and the x-ray source, the collimator comprising
        an x-ray blocking surface comprising a one-piece plate defining an aperture formed therethrough, the aperture defining an aperture edge, the x-ray blocking surface configured so that the one-piece plate prevents x-ray transmission and the aperture allows x-ray transmission therethrough, wherein a projection of the beam is projected proximate to the detector;
    wherein the aperture edge includes a first end portion including a first end of the aperture edge, a second end portion including a second end of the aperture edge, and a central portion including a center of the aperture edge, the central portion interposed between the first and second end portions, wherein the first end portion of the aperture edge corresponds to a first end portion of the detector, the second end portion of the aperture edge corresponds to a second end portion of the detector, and the central portion of the aperture edge corresponds to a central portion of the detector; and
    wherein a profile of the aperture edge is discontinuous at a point between the first end of the aperture edge and the center of the aperture edge.

10. The system of claim 9, wherein the profile of the aperture edge is discontinuous at a plurality of points between the first end of the aperture edge and the center of the aperture edge.

11. The system of claim 9, wherein the aperture edge comprises a linear portion and a curved portion joining the linear portion, wherein a joining point defining the location where the linear portion joins the curved portion defines a discontinuity of the aperture edge.

12. The system of claim 9, wherein the first end portion of the aperture edge includes a flat segment extending along a length of the aperture edge, and the central portion of the aperture edge includes a non-linear portion extending along the length of the aperture edge.

13. The system of claim 12, wherein the detector is curved along a direction transverse to a central projection of the beam, wherein the non-linear portion is configured to provide a first, substantially linear beam projection edge corresponding to the central portion of the detector, and wherein the flat segment is configured to provide a second beam projection edge that extends inwardly from the first, substantially linear beam projection in a lateral direction.

14. The system of claim 9, wherein the aperture edge includes a plurality of differently sloped linear segments interposed between the first end of the aperture edge and the center of the aperture edge.

15. The system of claim 9, wherein the central portion of the aperture edge is configured to provide a first beam projection substantially conforming with a profile of the central portion of the detector, and the first end portion of the aperture edge is configured to provide a second beam projection substantially differing with a profile of the first end portion of the detector.

16. The system of claim 9, wherein the detector comprises elements in the first end portion configured for measurement of flux of the beam.

17. The system of claim 9 further comprising a processor, the processor configured to reconstruct an image using information from the detector, wherein the processor is configured to use information received from the central portion of the detector to reconstruct the image and to use information from the first end of the detector to track a focal point of the beam.

18. A system comprising:
   an x-ray source, the x-ray source providing an x-ray beam;
   a detector, the detector receiving a portion of the x-ray beam;
   a collimator interposed between the detector and the x-ray source, the collimator comprising
      an x-ray blocking surface defining an aperture, the x-ray blocking surface comprising one or more generally flat plates defining an aperture edge of the aperture, the x-ray blocking surface configured so that the one or more generally flat plates prevent x-ray transmission and the aperture allows x-ray transmission therethrough, wherein a projection of the beam is projected proximate to the detector;
   wherein the aperture edge includes a first end portion including a first end of the aperture edge, a second end portion including a second end of the aperture edge, and a central portion including a center of the aperture edge, the central portion interposed between the first and second end portions, wherein the first end portion of the aperture edge corresponds to a first end portion of the detector, the second end portion of the aperture edge corresponds to a second end portion of the detector, and the central portion of the aperture edge corresponds to a central portion of the detector; and
   wherein the central portion of the aperture edge is configured to provide a first beam projection portion substantially conforming with a profile of the central portion of the detector, and the first end portion of the aperture edge is configured to provide a second beam projection portion substantially differing with a profile of the first end portion of the detector; and
   a processor configured to reconstruct an image using information provided by the detector, wherein information provided by the central portion of the detector is processed in a first manner including reconstruction of an image and information provided by the first end portion of the detector is processed in a second manner including tracking processing.

19. The system of claim 18, wherein the detector has a generally rectangular footprint and is curved along a direction transverse to a central projection of the beam, and wherein the first end portion of the aperture edge include a flat segment and the central portion of the aperture edge includes a non-linear portion.

20. The system of claim 19, wherein a joining point defining a location where the flat segment joins the non-linear portion defines a discontinuity of the aperture edge.

21. The system of claim 18, wherein the detector comprises a subgroup of elements configured to detect a flux of the second beam projection portion, the subgroup of elements positioned proximate to one or more edges of the detector.

* * * * *